United States Patent
Masket

(10) Patent No.: US 9,433,498 B2
(45) Date of Patent: Sep. 6, 2016

(54) ANTI-DYSPHOTOPIC INTRAOCULAR LENS AND METHOD

(71) Applicant: Samuel Masket, Venice, CA (US)

(72) Inventor: Samuel Masket, Venice, CA (US)

( * ) Notice: Subject to any disclaimer, the term of this patent is extended or adjusted under 35 U.S.C. 154(b) by 0 days.

(21) Appl. No.: 14/182,000

(22) Filed: Feb. 17, 2014

(65) Prior Publication Data

US 2014/0163676 A1    Jun. 12, 2014

Related U.S. Application Data

(62) Division of application No. 13/083,853, filed on Apr. 11, 2011, now Pat. No. 8,652,206.

(60) Provisional application No. 61/323,060, filed on Apr. 12, 2012.

(51) Int. Cl.
*A61F 2/16* (2006.01)

(52) U.S. Cl.
CPC ........... *A61F 2/1648* (2013.01); *A61F 2/1613* (2013.01); *A61F 2/1694* (2013.01); *A61F 2002/1699* (2015.04)

(58) Field of Classification Search
CPC .. A61F 2/1613; A61F 2/1616; A61F 2/1621; A61F 2/1648; A61F 2/1694; A61F 2002/1697; A61F 2002/1699
See application file for complete search history.

(56) References Cited

U.S. PATENT DOCUMENTS

| | | |
|---|---|---|
| 5,171,320 A | 12/1992 | Nishi |
| 5,266,074 A | 11/1993 | Nishi et al. |
| 5,716,403 A | 2/1998 | Tran et al. |
| 5,843,184 A | 12/1998 | Cionni |
| 6,027,531 A | 2/2000 | Tassignon |
| 6,200,342 B1 | 3/2001 | Tassignon |
| 2005/0187623 A1 | 8/2005 | Tassignon |
| 2007/0067031 A1 | 3/2007 | Das et al. |
| 2007/0123981 A1 | 5/2007 | Tassignon |
| 2007/0276482 A1 | 11/2007 | Coroneo |
| 2008/0269881 A1 | 10/2008 | Simpson et al. |
| 2008/0269882 A1 | 10/2008 | Simpson et al. |
| 2008/0269883 A1 | 10/2008 | Das et al. |
| 2008/0269884 A1 | 10/2008 | Vannoy |
| 2008/0269885 A1 | 10/2008 | Simpson et al. |
| 2008/0269889 A1 | 10/2008 | Simpson |
| 2008/0269890 A1 | 10/2008 | Simpson et al. |
| 2008/0269891 A1 | 10/2008 | Hong et al. |

FOREIGN PATENT DOCUMENTS

WO        03/077803 A1    9/2003

OTHER PUBLICATIONS

Okihiro Nishi, M.D. and Kayo Nishi, M.D., Accommodation Amplitude After Lens Refilling With Injectable Silicone by Sealing the Capsule With a Plug in Primates, Archives of Ophthalmology, vol. 116, Oct. 1998, pp. 1358-1361.

(Continued)

*Primary Examiner* — Howie Matthews
(74) *Attorney, Agent, or Firm* — Wood, Herron & Evans, LLP

(57) ABSTRACT

An intraocular lens implant includes a lens having an anterior portion, a posterior portion, and a circumferential edge located therebetween. An annular notch is formed in the anterior portion and oriented in an anteriorly-directed orientation.

23 Claims, 7 Drawing Sheets

(56) References Cited

OTHER PUBLICATIONS

Samuel Masket, M.D., Clinical Professor, Negative Dysphotopsia—What Works?, Presentation at David Geffen School of Medicine, UCLA on Mar. 9, 2010 (12 pages).
European Patent Office, International Search Report and Written Opinion of the International Searching Authority, International Application No. PCT/US2011/032054, mailed Jul. 6, 2011 (15 pages).
European Patent Office, Second Written Opinion of the International Search Authority, International Application No. PCT/US2011/032054, mailed May 8, 2012 (9 pages).
European Patent Office, Notification of Transmittal of the International Preliminary Report on Patentability, International Application No. PCT/US2011/032054, mailed Jun. 22, 2012 (19 pages).
European Patent Office, Examination Report, European Application No. 11716121.6, mailed Jul. 8, 2016 (4 pages).

ANTI-DYSPHOTOPIC INTRAOCULAR LENS AND METHOD

CROSS-REFERENCE TO RELATED APPLICATIONS

The present application is a divisional of U.S. patent application Ser. No. 13/083,853, filed on Apr. 11, 2011, now U.S. Pat. No. 8,652,206 and which claims the filing benefit of U.S. Provisional Patent Application Ser. No. 61/323,060, filed on Apr. 12, 2010, the disclosures of which are hereby incorporated herein by reference in their entireties.

FIELD OF THE INVENTION

This present invention relates generally to intraocular lens implants and, more particularly, to intraocular lens implants and surgical methods for reducing negative dysphotopsia.

BACKGROUND OF THE INVENTION

The human eye is the sensory organ for reacting to light. As shown in FIG. 1, the anatomical structure of an anterior segment of the eye 10 is shown and includes a transparent outer layer, the cornea 12, that is continuous with an opaque sclera 14 forming the lateral white portion of the eye 10. The cornea 12 encloses an anterior chamber 16 and posterior chamber 18, both filled with aqueous humor. The anterior and posterior chambers 16, 18 are separated by the iris 20, which is a circular, muscular structure that controls the diameter of the centrally-disposed pupil 22 and provides the color portion of the eye 10.

Light enters the eye 10 through the cornea 12, passes through the aqueous humor of the anterior chamber 16 and the pupil 22 to the lens 24. The lens 24 is a transparent, biconvex structure that focuses incoming light onto the retina (not shown). Suspensory ligaments, or zonules 26, suspend the lens 24 from ciliary bodies 28, which are muscular structures that contract to affect the convexity, i.e., shape, of the lens 24 and thereby adjust the focal distance of the eye 10. The lens 24 itself is comprised of an outer membrane, the capsular bag 30, surrounding a group of compressed cells, the nucleus 32, and a less dense compression of cells, the cortex 34.

Cataracts are a medical condition that is manifested as decreased transparency, or clouding, of the lens 24 within the eye 10. The clouding may occur to any portion of the lens 24, including the nucleus 32, the cortex 34 and/or the capsulor bag 30. Cataracts generally develop bilaterally, i.e., affecting both eyes, and to varying degrees ranging from a slight clouding to complete opacity and greatly reduce the transmission of light through the lens 24 to the retina (not shown). If left untreated, cataracts may result in blindness.

One surgical procedure for the treatment of cataracts, illustrated in FIGS. 2-4, is an Extra-Capsular ("ECCE") surgery that includes capsulorrhexis, or a partial removal of an anterior portion of the capsular bag 30. While not limiting, the capsulorrhexis may be created by cutting and may have a diameter of approximately 5 mm. The cortex 34 (FIG. 1) and the nucleus 32 (FIG. 1) portions of the lens 24 are removed through the opening, defined by a capsulorrhexis edge 38, while the remaining portion of the capsular bag 30 is retained. An intraocular lens ("IOL") 40 then replaces the cortex 34 (FIG. 1) and the nucleus 32 (FIG. 1).

The IOL 40, illustrated in greater detail in FIGS. 4A and 4B according to one embodiment, includes a transparent, biconvex structure 42 (though other lens structures may be used) constructed from a plastic, silicone, or acrylic material selected to replicate the refractive index and accommodation, or adjustable optical power, of the native lens 24 (FIG. 1). The biconvex structure 42 includes an anterior portion 44 and a posterior portion 46 that converge at a circumferential, lateral edge 48. While the circumferential edge 48 is specifically illustrated as a lateral wall, it would be understood that the length of the lateral wall may vary and may in fact be an edge of minimal thickness.

Two diametrically opposed haptic members 50 extend radially outwardly from the biconvex structure 42 and are generally oriented to be planar; however, angulated haptic members are also known and may be used if desired. The haptic members 50 are configured to engage the capsular bag 30 (FIG. 2) and to suspend the IOL 40 at a desired position. While the haptic members 50 are illustrated as radially extending projections, or arms, other embodiments and structures are known to those of ordinary skill in the art.

During cataract surgery, the placement of the IOL 40 may vary. For example, one conventional surgical method, shown in FIG. 2, positions the IOL 40 within the capsular bag 30 such that the haptic members 50 engage an inner surface of the wall of the capsular bag 30 and the IOL 40 is located generally centrally within the capsular bag 30. FIG. 3 illustrates an alternative position for the IOL 40, wherein the IOL 40 positioned within the posterior chamber 18 with the haptic members 50 extending into the ciliary sulcus 52.

Positioning the IOL 40 anterior to the capsular bag 30 within the posterior chamber 18 has several potential disadvantages, including possible decentralization of the IOL and/or posterior iris chafing. Thus, placement of the IOL 40 within the capsular bag 30 may be preferred. However, capsular bag fixation may result in negative dysphotopsia ("ND"), which is a visual phenomenon that occurs after an uncomplicated cataract surgery. Symptoms include a shadowing in the temporal field of vision.

The etiology of ND is unknown, but symptoms may be relieved with a second surgery, known as the piggyback method, which is illustrated in FIG. 4. As shown, the conventional piggyback method includes the first IOL, which was previously positioned within the capsular bag 30, and a second, later positioned IOL, which is placed anterior to the capsular bag 30 as shown in FIG. 4. This approach, while improving the symptoms of ND, may again lead to posterior iris chafing. Also, the alternative approach of placing both IOLs within the capsular bag may lead to interlenticular opacification ("ILO").

Thus, there exist a need for an IOL and surgical method that provides the benefits of a capsular bag fixation but does not result in ND.

SUMMARY OF THE INVENTION

The present invention overcomes the foregoing problems and other shortcomings, drawbacks, and challenges of conventional IOL designs and surgical methods associated with reducing the occurrence of ND. While the invention will be described in connection with certain embodiments, it will be understood that the invention is not limited to these embodiments. To the contrary, this invention includes all alternatives, modifications, and equivalents as may be included within the spirit and scope of the present invention.

In one embodiment of the present invention, an intraocular lens implant is provided including a lens having an anterior portion, a posterior portion, and a circumferential edge located between the anterior and posterior portions. An annular notch is formed in the anterior portion of the IOL and is oriented in an anteriorly-directed orientation.

According to another embodiment of the present invention, the IOL includes a lens having an anterior portion, a posterior portion, and a circumferential edge located between the anterior and posterior portions. At least two haptic members extend radially away from the lens and lie within a common plane. An annular notch is formed in the anterior portion of the IOL and is oriented in an anteriorly-directed orientation.

In yet another embodiment of the present invention, the IOL includes a posterior portion that is configured to reside within the capsular bag within an eye of a patient. An anterior portion of the IOL includes a first portion that is configured to be anterior to the capsular bag and within the ciliary sulcus. A second portion of the anterior portion is configured to reside within the capuslor bag. An annular notch is formed in the IOL, between the first and second portions of the anterior portion, and is configured to receive a capsulorrhexis edge of the capsular bag within the annular notch.

According to yet another embodiment of the present invention, an IOL is provided having a lens with an anterior portion, a posterior portion, and a circumferential edge between the anterior and posterior portions. An annular notch is formed in the anterior portion of the lens and is configured to capture a capsulorrhexis edge of the capsular bag within the annular notch.

According to another aspect of the present invention, a method of implanting an intraocular lens within an eye of a patient is provided. The method includes creating a capsulorrhexis within the capsular bag within an eye of a patient. The cortex and the nucleus of the lens are removed from the capsular bag. The intraocular lens is inserted into the capsular bag such that a posterior portion of the lens resides within the capsular bag, a first portion of an anterior portion is located anterior to the capsular bag and resides within the ciliary sulcus, a second portion of the anterior portion is located within the capsular bag, and an annular notch that is formed in the between the first and second portions of the anterior portion captures an edge of the capsulorrhexis within the annular notch.

The above and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
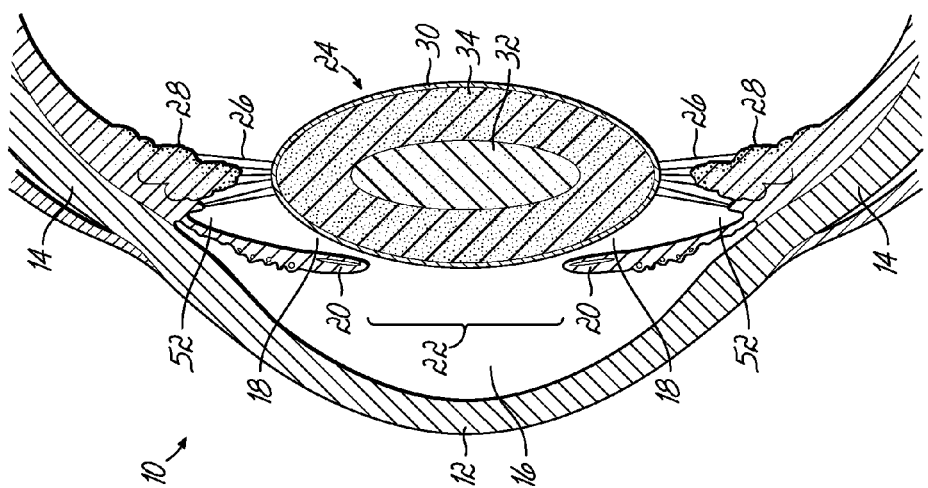
FIG. 1 is a cross-sectional view, in the sagittal plane, through an anterior segment of a healthy human eye.
Figure 4:
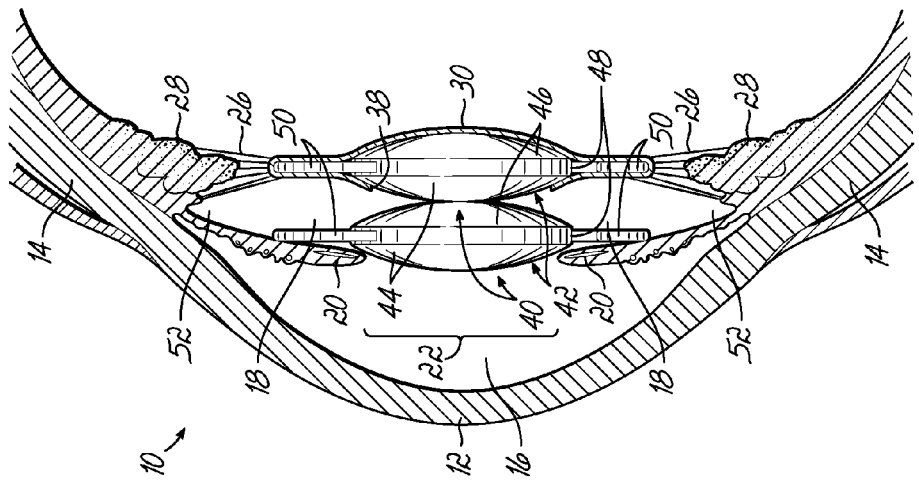
FIG. 4 is a cross-sectional view, in the sagittal plane, through an anterior segment of a human eye having a piggybacked IOL implant.
Figure 3:
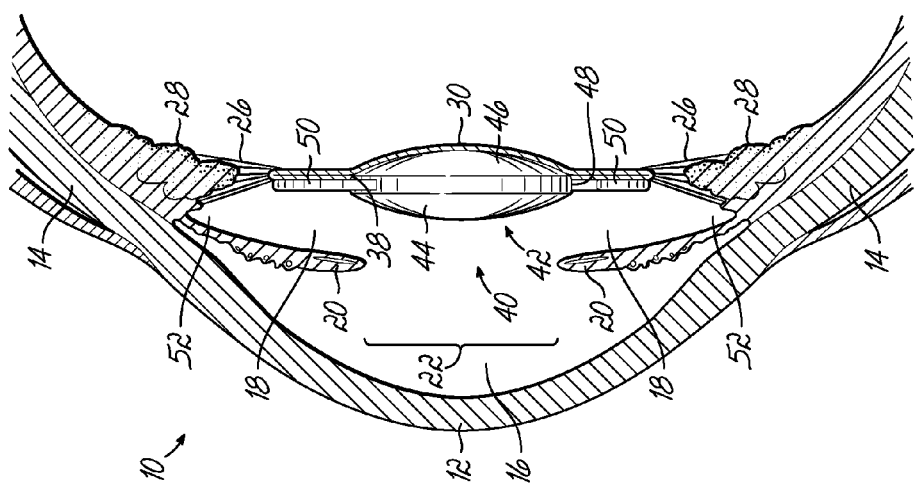
FIG. 3 is a cross-sectional view, in the sagittal plane, through an anterior segment of a human eye having an IOL implanted within the posterior chamber.
Figure 5B:
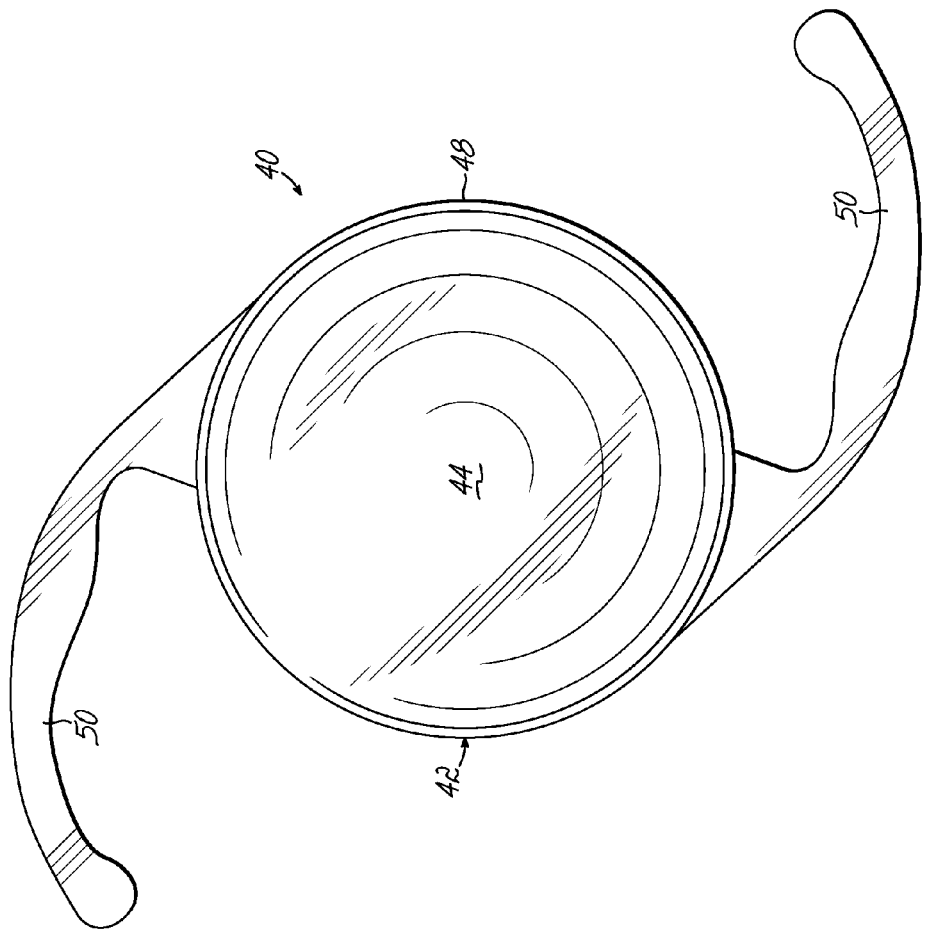
FIG. 5B is a top view of the IOL of FIG. 5A.
Figure 5A:
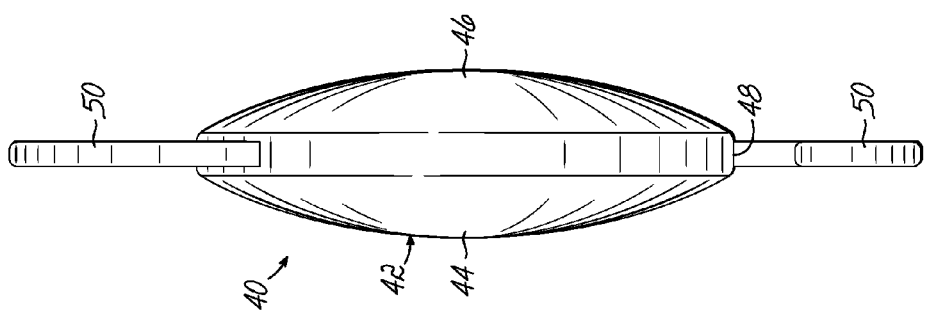
FIG. 5A is a side-elevational view of one embodiment of a conventional IOL.
Figure 6B:
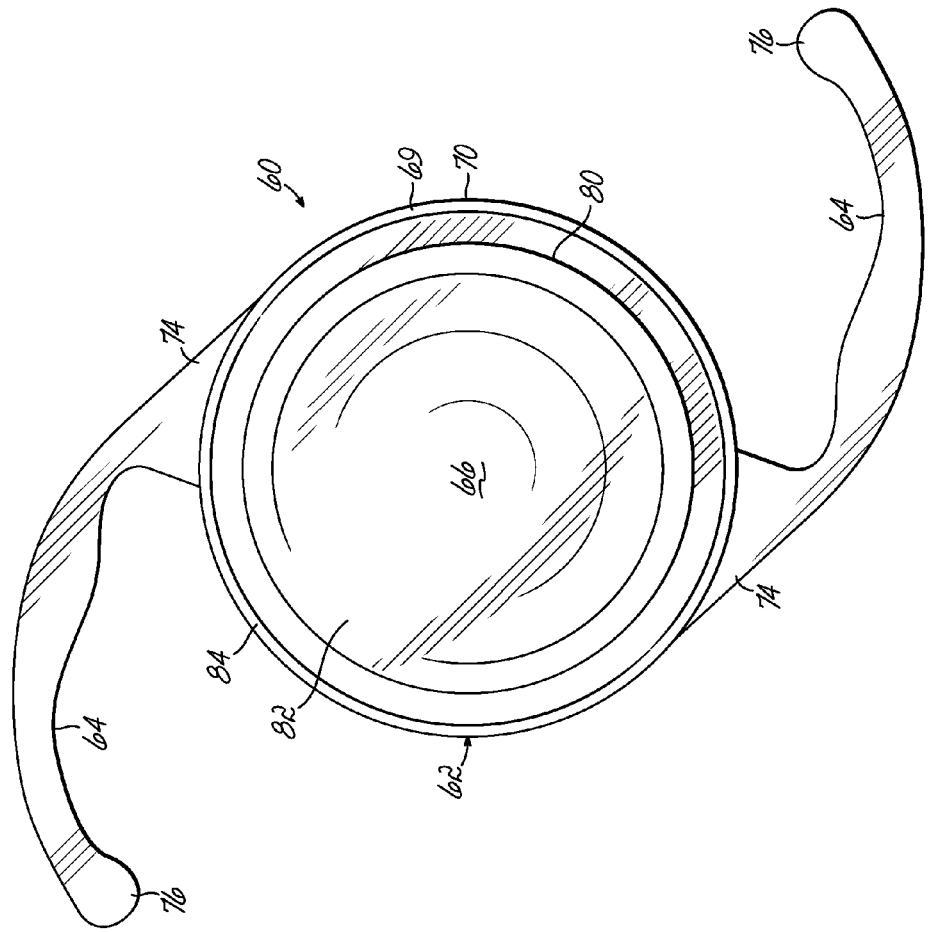
FIG. 6B is a top view of the IOL of FIG. 6A.
Figure 6A:
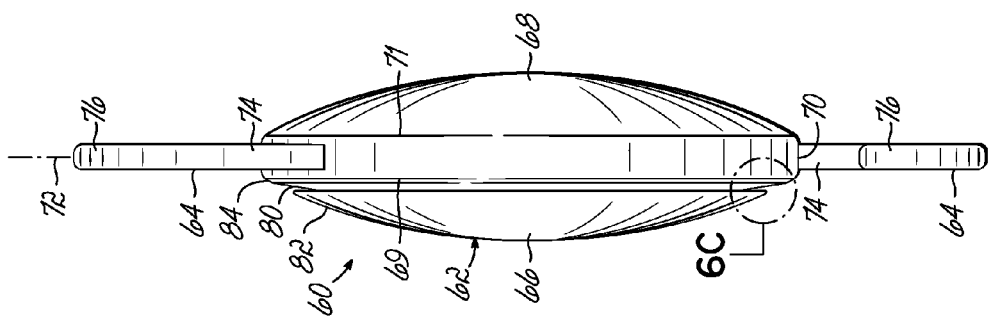
FIG. 6A is a side-elevational view of one embodiment of an IOL in accordance with the present invention.
Figure 7A:
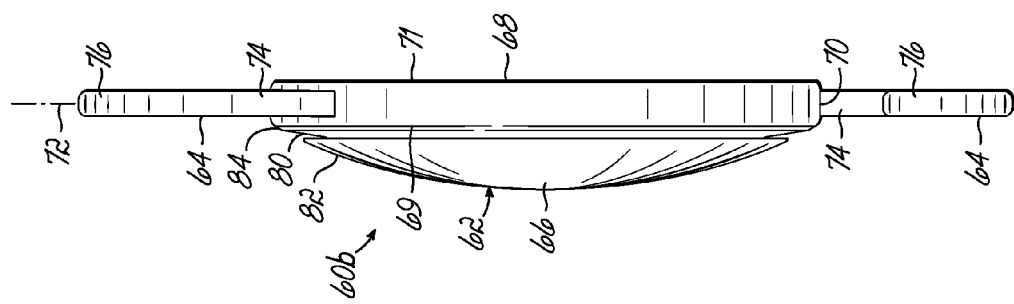
FIG. 7A is a side-elevational view of another embodiment of an IOL in accordance with the present invention.
Figure 7B:
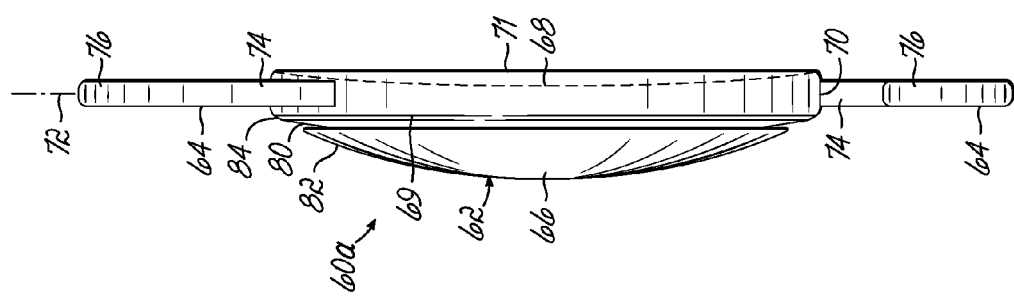
FIG. 7B is a side-elevational view of yet another embodiment of an IOL in accordance with the present invention.

Turning now to the figures, and to FIGS. 6A and 6B in particular, one embodiment of an IOL 60 in accordance with the present invention is shown. While the IOL 60 of FIGS. 6A and 6B is shown as a biconvex lens 62 having at least two diametrically opposed haptic members 64, other lens designs may also be used, including, for example, a convex-concave IOL 60a (FIG. 7A), a convex-planar IOL 60b (FIG. 7B), or other designs as desired. The biconvex lens 62 comprises a transparent structure constructed from a polymeric, silicone, acrylic, or other suitable moldable material having a refractive index similar to the native lens 24 (FIG. 1). Anterior and posterior portions 66, 68 of the biconvex lens 62 converge at a lateral, circumferential edge 70 of the IOL 60. As shown, the circumferential edge 70 may be a wall having a length of about 1 mm with an anterior edge 69 and a posterior edge 71. However, in some embodiments, the anterior and posterior portions 66, 68 may converge at a common edge (not shown). When the IOL 60 is biconvex and the anterior portion 66 and the posterior portion 68 converge at this common edge and are substantially similar in size and shape (a symmetric biconvex lens), the circumferential edge 70 may coincide with an equatorial plane; however, the biconvex lens may also be asymmetric, for example, where the anterior portion 66 has a convexity that is greater than a convexity of the posterior portion 68.

In some embodiments, the surface of either portion 66, 68 of the biconvex lens 62 may be constructed to have uniform optical properties across its diametric surface or it may be constructed as a multi-focal or accommodating lens having two or more zones of differing optical properties.

The two or more haptic members 64 may extend radially outwardly from the biconvex lens 62 and are generally positioned to lie within a common plane 72 (i.e., are planar) extending through the biconvex lens 62 as shown in FIG. 6A. Although not shown, the haptic members 64 may also be angulated relative to the common plane 72. In some embodiments, the common plane 72 is coincident with the circumferential edge 70 of the biconvex lens 62. That is, the common plane 72 may be substantially co-planar with a diameter of the IOL 60 and positioned between the anterior and posterior edges 69, 71. When the IOL 60 is a symmetric biconvex lens and the anterior and posterior portions 66, 68 are similar in size and shape, the biconvex lens 62 is symmetric about the equatorial plane and the common plane 72 may be positioned equidistant from the anterior and posterior edges 69, 71 (or at the converged edges of the anterior and posterior portions 66, 68) at the equatorial plane.

Figure 2:
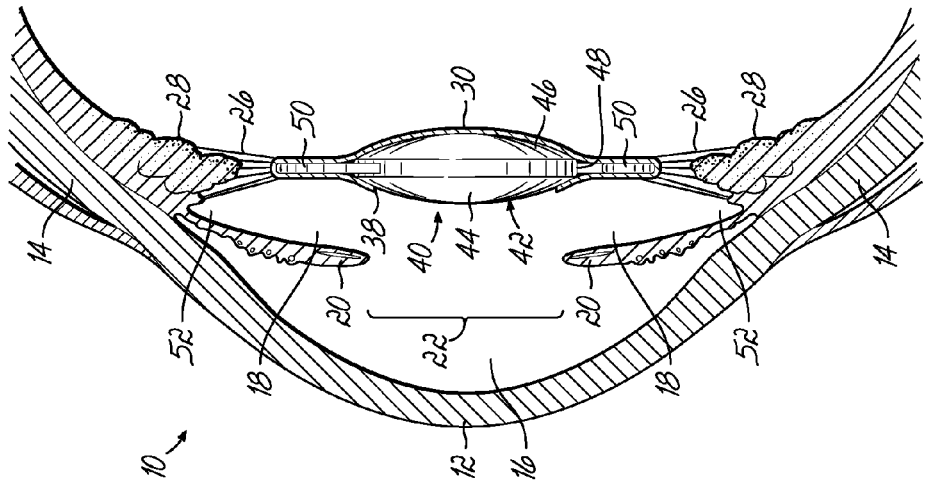
FIG. 2 is a cross-sectional view, in the sagittal plane, through an anterior segment of a human eye having an IOL implanted within the capsular bag.

The haptic members 64 may be constructed from a pliable material, such as a polymer, extruded poly(methyl methacrylate) ("PMMA"), polypropylene, silicone, or acrylic. The pliable material allows the haptic members 64 to be folded for insertion through the capsulorrhexis edge 38 (FIG. 2) and deployment within the capsular bag 30 (FIG. 1). In some embodiments, the haptic members 64 may be constructed from the same material as the biconvex lens 62, and indeed the IOL 60 may be a unitary structure; however, this is not necessary. In still other embodiments, the haptic members 64 may alternatively be constructed from sturdy treads or filaments that are attached to, or embedded within, the biconvex lens 62 and extend outwardly along the common plane 72.

In the specific illustrated embodiment, the haptic members 64 include an enlarged base 74, adjacent the biconvex lens 62, with radially extending projections or arms 76. The radially outward construction of the haptic members 64 is configured to accommodate anatomical size differences of different patients. That is, the inside walls of a capsular bag 30 having a diameter that is smaller than the larger dimension of the IOL (i.e., the diameter extending along the common plane 72 and across the haptic members 64) will cause the arms 76 to be deflected radially inwardly. Thus, a larger diameter capsular bag 30 would cause less radially inward deflection of the arms 76 than the smaller diameter capsular bag 30.

The biconvex lens 62 in accordance with one embodiment of the present invention includes an annular groove 80 that is positioned anterior to the common plane 72 defined by the haptic members 64. The annular groove 80 may be positioned anteriorly of the circumferential edge 70, for example about 0.2 mm to about 1 mm, or alternatively between about 0.25 mm and about 0.75 mm, of the anterior edge 69 of the circumferential edge 70.

Figure 6D:
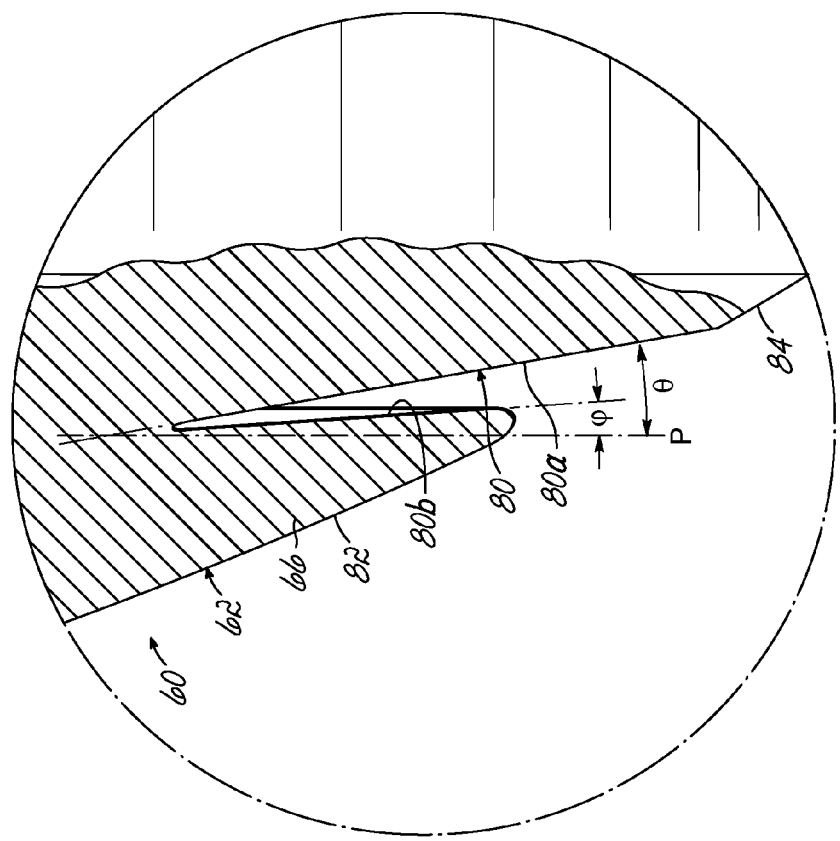
FIG. 6D is a cross-sectional view that is similar to FIG. 6C and showing an IOL according to an alternative embodiment of the present invention.
Figure 6C:
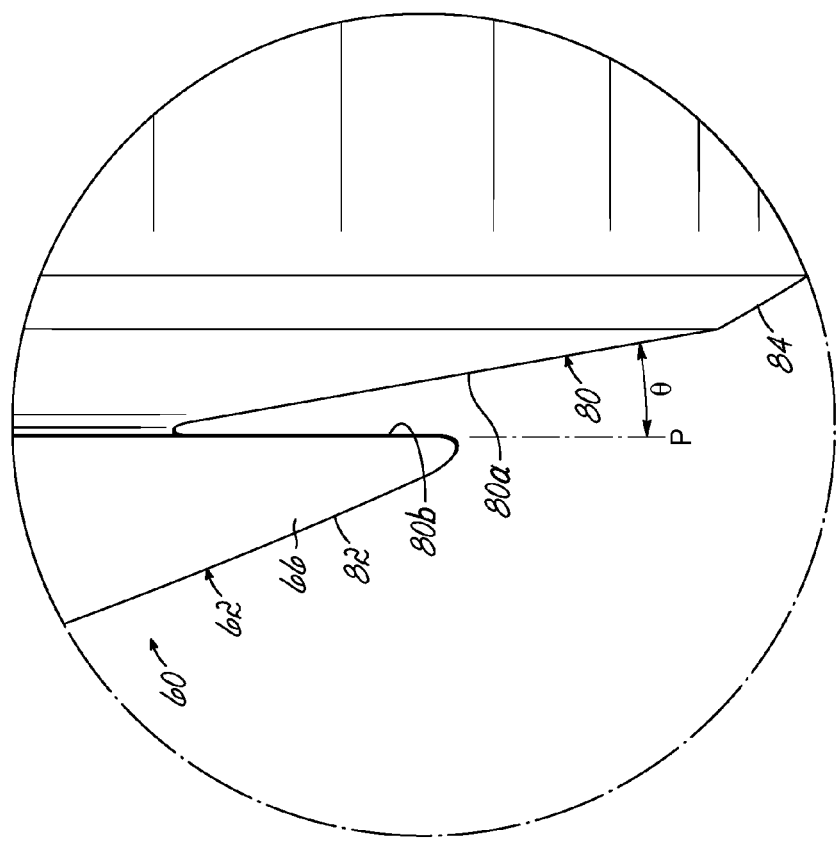
FIG. 6C is an enlarged, side-elevational view of the encircled area 6A of the IOL in FIG. 6A.

Furthermore, and as more specifically shown in FIGS. 6C and 6D, the annular groove 80 includes a posterior wall 80a and an anterior wall 80b. In one embodiment, the posterior wall 80a of the annular groove 80 may lie, in cross-section, on a plane that is disposed at a first angle, $\theta$, relative to a horizontal plane (represented by "P"), which may range from about 10° to about 25°. The anterior wall 80b of the annular groove 80 may lie, in cross-section, in a plane that is disposed at an angle, $\phi$, relative to the horizontal plane, P, which may range from about 0° (e.g., substantially horizontal) to about 10°.

While the groove 80 may be specifically configured to the particular anatomical shape as appropriate in order to capture and secure the capsulorrhexis edge 38 (FIG. 2), the particular groove 80 illustrated in FIG. 6A extends inwardly into the lens 62 about 0.5 mm. Other dimensions are possible and may depend on the dimensions of the capsulorrhexis preferred by the surgeon. The annular groove 80 may be machined, such as by laser cutting, into the previously molded biconvex lens 62 or may be included during the molding process.

Figure 8:
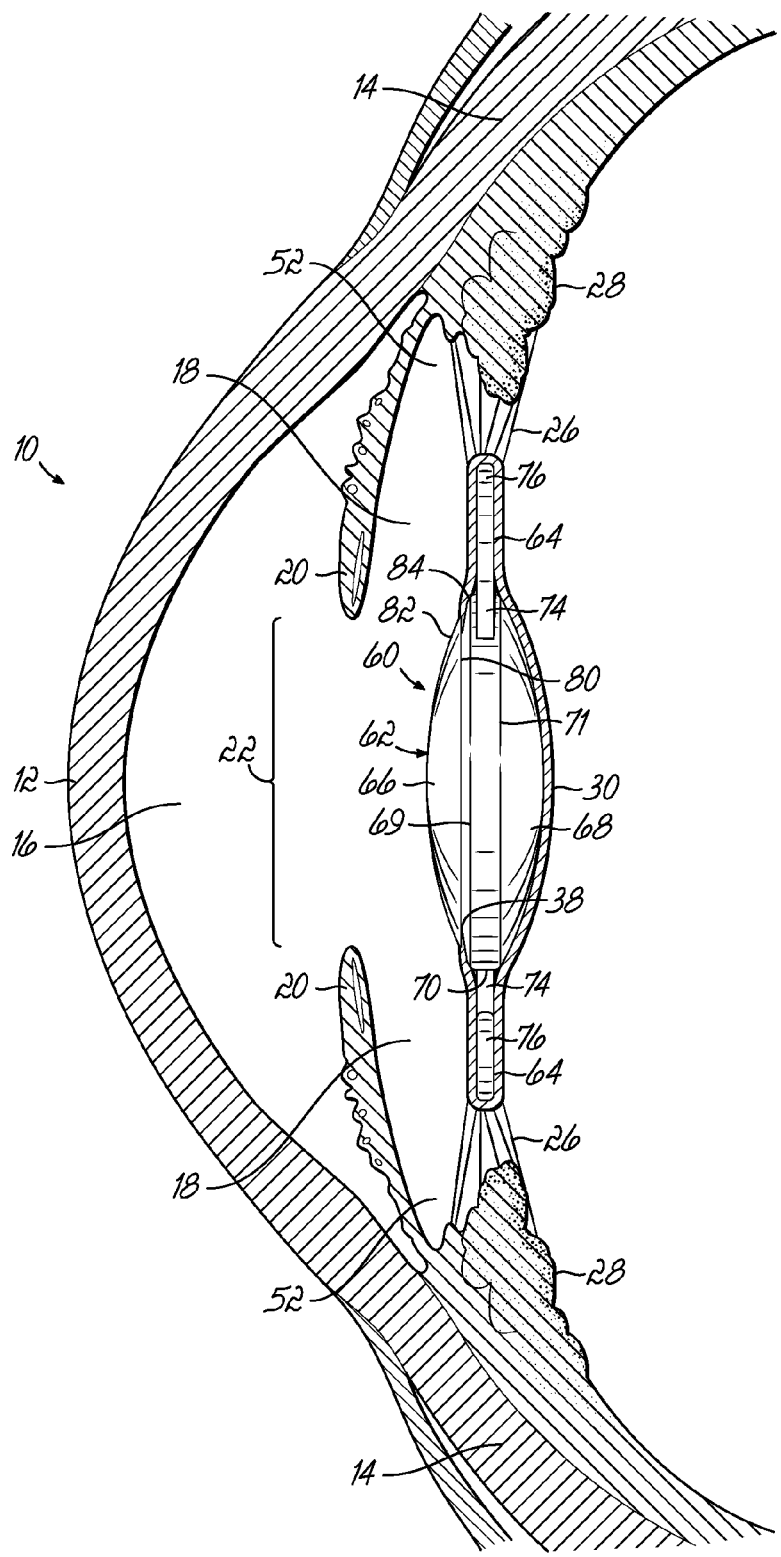
FIG. 8 is a cross-sectional view, in the sagittal plane, through an anterior segment of a human eye having the IOL of FIG. 6 implanted within the capsular bag.

In use, and with reference now to FIG. 8, the surgeon creates the capsulorrhexis within the capsular bag 30 using a punch, a laser, or another appropriate cutting device. While the shape and the diameter of the capsulorrhexis may vary, generally the capsulorrhexis is circular or semi-circular in shape and has a diameter of approximately 5 mm. The surgeon then removes the cortex 34 (FIG. 1) and the nucleus 32 (FIG. 1) of the native lens 24 (FIG. 1) through the capsulorrhexis. The native lens may include a cataract or may be crystalline; however, the method described herein generally refers to cataract surgeries. The IOL 60 is then inserted through the capsulorrhexis and into the capsular bag 30. Inserting may include deployment of the IOL 60 from a folded state contained within a delivery device, such as a cannula. Otherwise, during insertion, the IOL 60 may capture the capsulorrhexis edge 38. Alternatively, insertion of the IOL 38 may occur within the volume contained by the capsular bag 30, and the anterior portion 66 of the IOL 60 having the annular groove 80 therein may be partially retracted through the capsulorrhexis such that the capsulorrhexis edge 38 is captured and retained by the annular groove 80. The haptic members 64 extend radially within the capsular bag 30 and engage the inner surface of the capsular bag 30.

With the surgical process complete, the capsulorrhexis edge 38 is captured by the groove 80 such that a first portion 82 of the anterior portion 66 of the IOL 60 is external to the capsular bag 30 and within the posterior chamber 18 and a second portion 84 of the anterior portion 66 is within the capsular bag 30. The posterior portion 68 of the IOL and the haptic members 64 are also within the capsular bag 30. Thus, the patient having cataract surgery in accordance with an embodiment of this invention, would receive the benefits generally achievable by capsular bag placement of the IOL, i.e., reduced occurrence of iris chafing and/or decentralization associated placement of the entire IOL, or a large portion of the IOL, with a posterior chamber 18. Furthermore, the patient would receive the benefit of reduced of ND. While not wishing to be bound by theory, it is believed that the reduction in ND may be attributed to having an optic edge of the lens cover the capsulorrhexis edge.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. An intraocular lens implant for implantation within a capsular bag formed with a capsulorrhexis defining a capsulorrhexis edge, comprising:

a lens having a convex anterior optical portion including a first convex portion and a second portion, and a posterior optical portion, the convex anterior optical portion and the posterior optical portion being located on opposite anterior and posterior sides, respectively, of a single circumferential edge of the lens, with the circumferential edge being positioned at and forming a single maximum diameter of the lens, the circumferential edge being defined by a single annular wall having an axial length and extending between an anterior edge and a posterior edge, with the anterior edge and the posterior edge being spaced apart by the length;

an annular groove formed in the convex anterior optical portion between the first convex portion and the second portion and being defined by an anterior wall and a posterior wall, with the second portion extending radially inwardly from the anterior edge of the annular wall and the entire annular groove being positioned anteriorly of the annular wall and extending from a surface of the convex anterior optical portion and being configured to receive the capsulorrhexis edge, and
a haptic member extending outwardly from the circumferential edge.

2. The intraocular lens of claim 1, wherein the posterior optical portion is convex.

3. The intraocular lens implant of claim 2, wherein the convex anterior and convex posterior optical portions are symmetric.

4. The intraocular lens implant of claim 1, further comprising:
at least two haptic members extending radially away from the lens.

5. The intraocular lens implant of claim 4, wherein the at least two haptic members radially extend from the circumferential edge and lie in a common plane.

6. The intraocular lens implant of claim 5, wherein the common plane resides along the circumferential edge.

7. The intraocular lens implant of claim 1, wherein the annular groove is positioned about 0.2 mm to about 1 mm anteriorly of the circumferential edge.

8. The intraocular lens implant of claim 1, wherein the posterior wall of the annular groove lies, in cross-section, on a plane that is disposed at an angle relative to a horizontal plane that is perpendicular to an optical axis of the lens from about 10° to about 25°.

9. The intraocular lens implant of claim 1, wherein the anterior wall of the annular groove lies, in cross-section, on a plane that is disposed at an angle relative to a horizontal plane that is perpendicular to an optical axis of the lens from about 0° to about 10°.

10. An intraocular lens implant for implantation within a capsular bag formed with a capsulorrhexis defining a capsulorrhexis edge, comprising:
a lens having a convex anterior optical portion including a first convex portion and second portion, and a posterior optical portion, the convex anterior optical portion and the posterior optical portion being located on opposite anterior and posterior sides, respectively, of a single circumferential edge of the lens, with the circumferential edge being positioned at and forming a single maximum diameter of the lens, the circumferential edge being defined by a single annular wall having an axial length and extending between an anterior edge and a posterior edge, with the anterior edge and the posterior edge being spaced apart by the length;
at least two haptic members extending radially away from the lens and configured to lie within a common plane; and
an annular groove formed in the convex anterior optical portion between the first convex portion and the second portion and being defined by an anterior wall and a posterior wall, with the second portion extending radially inwardly from the anterior edge of the annular wall and the entire annular groove being positioned anteriorly of the annular wall and extending in an anteriorly-directed orientation from a surface of the convex anterior optical portion and being configured to receive the capsulorrhexis edge.

11. The intraocular lens of claim 10, wherein the posterior optical portion is convex.

12. The intraocular lens implant of claim 11, wherein the convex anterior and convex posterior optical portions are symmetric.

13. The intraocular lens implant of claim 10, wherein the common plane lies along the circumferential edge.

14. The intraocular lens implant of claim 10, wherein the annular groove is positioned about 0.2 mm to about 1 mm anteriorly of the circumferential edge.

15. The intraocular lens implant of claim 10, wherein the posterior wall of the annular groove lies, in cross-section, on a plane that is disposed at an angle relative to a horizontal plane that is perpendicular to an optical axis of the lens from about 10° to about 25°.

16. The intraocular lens implant of claim 10, wherein the anterior wall of the annular groove lies, in cross-section, on a plane that is disposed at an angle relative to a horizontal plane that is perpendicular to an optical axis of the lens from about 0° to about 10°.

17. The intraocular lens implant of claim 1, wherein the groove extends in an anteriorly-directed orientation.

18. The intraocular lens implant of claim 1, wherein the posterior wall extends in an anteriorly-directed orientation.

19. The intraocular lens implant of claim 1, wherein each of the anterior wall and the posterior wall extends in an anteriorly-directed orientation.

20. The intraocular lens implant of claim 10, wherein the posterior wall extends in an anteriorly-directed orientation.

21. The intraocular lens implant of claim 10, wherein each of the anterior wall and the posterior wall extends in an anteriorly-directed orientation.

22. The intraocular lens implant of claim 2, wherein the convex anterior and convex posterior optical portions are asymmetric.

23. The intraocular lens implant of claim 11, wherein the convex anterior and convex posterior optical portions are asymmetric.

* * * * *